(12) United States Patent  
Fernandez

(10) Patent No.: US 8,771,765 B1  
(45) Date of Patent: Jul. 8, 2014

(54) METHOD AND COMPOSITION FOR TREATMENT OF HAIR LOSS

(76) Inventor: Ailin Fernandez, Miami, FL (US)

( * ) Notice: Subject to any disclaimer, the term of this patent is extended or adjusted under 35 U.S.C. 154(b) by 55 days.

(21) Appl. No.: 12/644,192

(22) Filed: Dec. 22, 2009

(51) Int. Cl.
*A61K 36/47* (2006.01)
*A61K 36/61* (2006.01)
*A61K 36/534* (2006.01)

(52) U.S. Cl.
USPC .......................... 424/731; 424/742; 424/747

(58) Field of Classification Search
None
See application file for complete search history.

(56) References Cited

U.S. PATENT DOCUMENTS 4,945,094 A * 7/1990 Salim ........................ 514/263.31
5,401,503 A * 3/1995 Murayama .................... 424/773
6,465,514 B1 * 10/2002 Hallam et al. ................ 514/535

FOREIGN PATENT DOCUMENTS

KR 2006131106 A * 12/2006

OTHER PUBLICATIONS

Hairloss-reversible.com: Hair on Pillow. Dec. 31, 2004. Retrieved from the internet. <http://www.hairloss-reversible.com/discus/messages/1/158.html?1152852300>. Retrieved on May 22, 2011. 2 Pages.*
hairlicious.com. Retrieved from the internet on May 1, 2012. <http://www.hairliciousinc.com/2008/09/hair-question-how-to-treat-thinning.html>. Oct. 8, 2008. 7 Pages.*
healingwireforum.com. Retrieved from the internet on May 6, 2012. <http://www.healingwiseforum.com/viewtopic.php?f=11&t=3021>. 4 Pages.*

* cited by examiner

*Primary Examiner* — Susan Hoffman
(74) *Attorney, Agent, or Firm* — Sanchelima & Associates, P.A.

(57) ABSTRACT

A composition and method for treating hair loss including glyceride of ricinus oil, eucalyptol, and mint oil. The treatment method includes the use of this composition periodically (three times per week) for a predetermined period of time (typically one month). The composition cleans the follicular area, reducing the concentration of DHT (dihydrotestosterone), thereby stimulating the growth of hair.

3 Claims, No Drawings

METHOD AND COMPOSITION FOR TREATMENT OF HAIR LOSS

BACKGROUND OF THE INVENTION

1. Field of the Invention

The present invention relates to a method and composition for the treatment of hair loss, such as androgenetic alopecia and alopecia greata.

2. Description of the Related Art

Alopecia is the general term referring to any disease or condition involving hair loss. There are several different types of hair loss, the most common being androgenetic alopecia (AGA; see Sawaya, M. E. Seminars in Cutaneous Medicine and Surgery 17(4):276-283, 1998), alopecia greata (AA; see Fiedler & Alaiti, Dermatologic Clinics 14(4): 733-738, 1996, as well as chemotherapy and drug-induced alopecia.

Androgenetic alopecia (AGA) is by far the most common type of alopecia. AGA is a patterned, progressive loss of an excessive amount of hair from the scalp. Significant AGA occurs in 50% of men by the age of fifty and 50% of women by the age of sixty.

None of the compositions used in the prior art include the use of glyceride of ricinus oil (the botanical name is *ricinus communis*), eucalyptol, and mint oil. It has been found that these ingredients, when properly used inhibit hair loss, or significantly retard it.

A study was conducted by the applicant with the help of a laboratory, using 178 individuals. The composition and method of using the composition as claimed, was administered to these individuals. Favorable results were obtained in 98% of the cases within the first six weeks.

SUMMARY OF THE INVENTION

It is one of the objects of this invention to provide a composition and treatment method that can be used to delay the loss of hair.

It is yet another object of this invention to provide such a method and composition that is inexpensive to produce while retaining its effectiveness.

Further objects of the invention will be brought out in the following part of the specification, wherein detailed description is for the purpose of fully disclosing the invention without placing limitations thereon.

DETAILED DESCRIPTION OF THE INVENTION

The present invention includes a method and composition for treating hair loss in humans. The composition has the following active ingredients: ricinus oil, eucalyptol oil, and mint oil. Ricinus oil is also known as castor oil which is a plant extract consisting primarily of ricinoleic acid or ricinic acid ($C_{18}H_{32}O_2$). Eucalyptol ($C_{10}H_{18}O$) comprises up to 90 percent of the essential oil of some species of the generic product eucalyptus oil. Eucalyptol is also known by a variety of synonyms, such as 1,8-cineol, limonene oxide, cajeputol, eucalyptole, cineol, cineole, and 1-8 epoxy-p-methane. Mint oil's chemical constitution includes menthol, menthyl acetate, carvone, menthone, carvacrol, and limonene.

In one of the embodiments, the composition formula includes the following ingredients:
A) Glyceride of ricinus oil between 95.7% and 96.1%, in weight.
B) Eucalyptol between 1.95% and 2.00%, in weight.
C) Mint oil between 1.93% and 2.00%, in weight.

In one of the embodiments, the method comprises the steps of:
A) Identifying the area of the scalp to be treated. The scalp and hair should not be wet.
B) Applying a sufficient amount of the above-described composition, causing it to penetrate the scalp area for at least two hours. In one of the treatments, preferably after the first two, the composition is allowed to stay in contact with the scalp area being treated for a longer period of time. It has been found that leaving the composition overnight, at least one time, has provided good results.
C) Repeating the process, preferably three times per week, for at least one month. The previous step is discontinued upon achieving predetermined hair growth objectives.

To determine whether predetermined hair growth objectives are reached, the number of hairs in a given area is determined before initiating the treatment and subsequently compared. This is customary in the field and typically done by taking pictures over time. A user decides when he/she has achieved the desired objective.

It has been found that better results have been obtained when the composition is allowed to be in contact, one time, for an extended period of time, such as overnight, after being rubbed for 2 to 3 minutes to achieve deep penetration in the hair follicle.

The composition unclogs or cleans the follicular area, reducing the concentration of DHT (dihydro-testosterone), thereby stimulating the growth of hair. The eucalyptol opens or dilates the hair follicle to permit the glyceride of ricinus oil to clean the hair duct. The hair follicle tends to constrain its passage with the concentration of the DHT hormones. This prevents the normal growth of hair. Keeping the hair follicle clean with the composition subject of this invention permits the hair to grow again.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A method for treating hair loss on the scalp of a human being comprising the steps of:
   A) identifying an area on the scalp of a human being in need of treatment for hair loss, said area kept dry;
   B) applying a composition that consists essentially of glyceride of ricinus oil between 95.7% and 96.1% in weight, eucalyptol between 1.95% and 2.00% in weight, and mint oil between 1.93% and 2.00% in weight, to said area at least three times per week for a period of at least one month; and
   C) monitoring the progress of the growth of hair on said area.

2. The method set forth in claim 1 wherein the step of applying said composition includes rubbing said composition on the scalp area being treated for at least two minutes.

3. The method set forth in claim 2 further including the step of:
   D) applying said composition on the area of the scalp being treated for an extended period of time and not less than six hours but not more than twenty five hours per week.

* * * * *